United States Patent
Ertel

(12) 
(10) Patent No.: US 6,530,689 B2
(45) Date of Patent: Mar. 11, 2003

(54) UNIT WITH AN ADJUSTABLE CARRYING ARRANGEMENT

(75) Inventor: Rainer Ertel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/740,318

(22) Filed: Dec. 18, 2000

(65) Prior Publication Data

US 2001/0012332 A1 Aug. 9, 2001

(30) Foreign Application Priority Data

Dec. 17, 1999 (DE) .......................... 199 61 094

(51) Int. Cl.⁷ ................................. A61B 6/02
(52) U.S. Cl. ....................... 378/197; 378/193
(58) Field of Search ................. 378/193, 195, 378/196, 197, 198, 204, 205; 403/13, 14, 52, 59, 79, 80; 248/279.1, 285.1, 287.1

(56) References Cited

U.S. PATENT DOCUMENTS

| 2,110,764 A | * | 3/1938 | Graves ........................ 378/197 |
| 5,450,466 A | * | 9/1995 | Kadowaki et al. .......... 378/189 |
| 5,835,557 A | * | 11/1998 | Malmstrom ................. 378/193 |
| 5,838,764 A | * | 11/1998 | Saffer et al. ................. 378/197 |

FOREIGN PATENT DOCUMENTS

| DE | 42 37 013 | 5/1994 |
| DE | 197 02 829 | 7/1998 |
| DE | 197 25 457 | 12/1998 |
| EP | 0 624 543 | 11/1994 |

* cited by examiner

Primary Examiner—David P. Porta
(74) Attorney, Agent, or Firm—Schiff Hardin & Waite

(57) ABSTRACT

A unit has a bearing part and a carrying arrangement which is mounted by a mounting side on the bearing part so that it can be adjusted relative to the bearing part. The carrying arrangement is provided with a handle for the manual adjustment of the carrying arrangement relative to the bearing part. The handle is arranged on the mounting side of the carrying arrangement.

16 Claims, 4 Drawing Sheets

UNIT WITH AN ADJUSTABLE CARRYING ARRANGEMENT

BACKGROUND OF THE INVENTION

The present invention is directed to a unit having a bearing part and a carrying arrangement which is mounted by a mounting side on the bearing part so that it can be adjusted relative to the bearing part. The carrying arrangement is provided with a handle for the manual adjustment of the carrying arrangement relative to the bearing part.

A unit of the type having a bearing part and a carrying arrangement is a C-arm X-ray unit, such as described in German 197 02 829 A1 or German 197 25 457 A1. The C-arm of the X-ray unit, which are supports an X-ray source and an X-ray receiver, is mounted against a bearing part of an X-ray unit so that it can be adjusted along a circumference of the C-arm. For the manual adjustment of the C-arm along the circumference relative to the bearing part, a handle is arranged on a side surface of the C-arm, usually in the region where the X-ray receiver is provided. It is thus possible for the receiver, during adjustment of the C-arm, to move laterally past the bearing part.

The arrangement of the handle on the side surface of the C-arm has a disadvantage because the handle adds to the width of the C-arm and, as a result of which operation of the X-ray unit may be obstructed. In addition, when the X-ray unit is placed in a sterile environment, for example in an operating room, problems will occur with the sterile covering of the C-arm by a sterile sheet material, since, if the C-arm is covered, the handle is also covered by the sheet material, which adversely affects the accessibility of the handle.

German 42 37 013 A1 discloses a C-arm X-ray unit of which the C-arm, which is provided with an X-ray source and an image-recording system, can be adjusted relative to a bearing part (which is not completely illustrated) with the assistance of a motor. A handle, which is arranged on an image-recording system and is connected to an electrical motor, is provided for the adjustment of the C-arm relative to the bearing part.

In addition, German 43 16 011 A1 describes an arrangement which is intended for accommodating, transporting and positioning vehicles and has a bearing part and a carrying arrangement which is mounted by a mounting side on the bearing part such that it can be adjusted relative to the bearing part. The adjustment of the carrying arrangement relative to the bearing part takes place by means of a drive, which has a driven pinion pair engaged in a rack arrangement on the carrying arrangement.

SUMMARY OF THE INVENTION

The object of the present invention is to provide a carrying unit which can be adjusted relative to a bearing part which is designed so that obstructions by the handle are avoided during use of the unit.

According to the invention, this object is achieved by a unit having a bearing part and a carrying arrangement, which is mounted by a mounting side on the bearing part so that it can be adjusted relative to the bearing part. The carrying arrangement is provided with a handle for the manual adjustment of the carrying arrangement relative to the bearing part and the handle is arranged on the mounting side of the carrying arrangement. By virtue of the handle being arranged on the mounting side of the carrying arrangement, the handle no longer adds to the width of the carrying arrangement and, thus, allows avoiding any obstructions which would occur during operation of the unit if the handle were arranged laterally. Since, in the case of the carrying arrangement being covered, the mounting side of the carrying arrangement is not provided with the covering, in order to allow the adjustment of the carrying arrangement relative to the bearing part, it is also the case that the handle is not masked by the covering and is, thus, accessible to an operator without obstructions and limitations. The mounting side of the carrying arrangement is also intended to be understood as the side of the carrying arrangement which interacts with the bearing part of the unit during adjustments of the carrying arrangement relative to the bearing part. Accordingly, the handle is located on the side of the carrying arrangement which is in engagement with the bearing part.

A particularly preferred embodiment of the invention provides for the bearing part to be designed so that during adjustments of the carrying arrangement relative to the bearing part, the handle can run or pass through the bearing part. For this purpose, the bearing part preferably has a cutout of a size which allows the handle to be guided through the bearing part.

According to a variant of the invention, the handle is designed so that it can be displaced along the mounting side of the carrying arrangement. In this case, the handle is preferably adjusted along rails running along the mounting side and is provided with means which allow the handle to be arrested or secured on the rails. In this way, the handle can be adjusted in a user-specific manner on the carrying arrangement for the adjustment of the carrying arrangement relative to the bearing part.

An embodiment of the invention provides for the unit to be a medical unit, preferably an X-ray unit equipped with a C-arm. If, according to a variation of the invention, the handle is arranged at least essentially centrally on the mounting side of the carrying arrangement, for example on the outer circumference side of the C-arm, the handle, even following a sterile covering of the C-arm for use of the C-arm X-ray unit in a sterile environment, is accessible without limitation since, for reasons of ensuring the adjustability of the C-arm relative to the bearing part, the outer circumference side of the C-arm is not provided with the covering.

One embodiment of the invention provides for the handle to extend along the mounting side, the handle being designed, according to a variation of the invention, as a handle surface. Otherwise, in the case of a bearing part with a cutout for the through-passage of the handle, parts of an operator's body could pass between a handle end and the bearing part or, in the case of a handle provided with webs, between the web of the handle and the bearing part, which, on account of the moment of inertia of the C-arm during the adjustment of the C-arm relative to the bearing part, could result in body parts being caught or even severed.

Other advantages and features of the invention will be readily apparent from the following description of the preferred embodiments, the drawings and claims.

DESCRIPTION OF THE PREFERRED EMBODIMENTS

Figure 1:
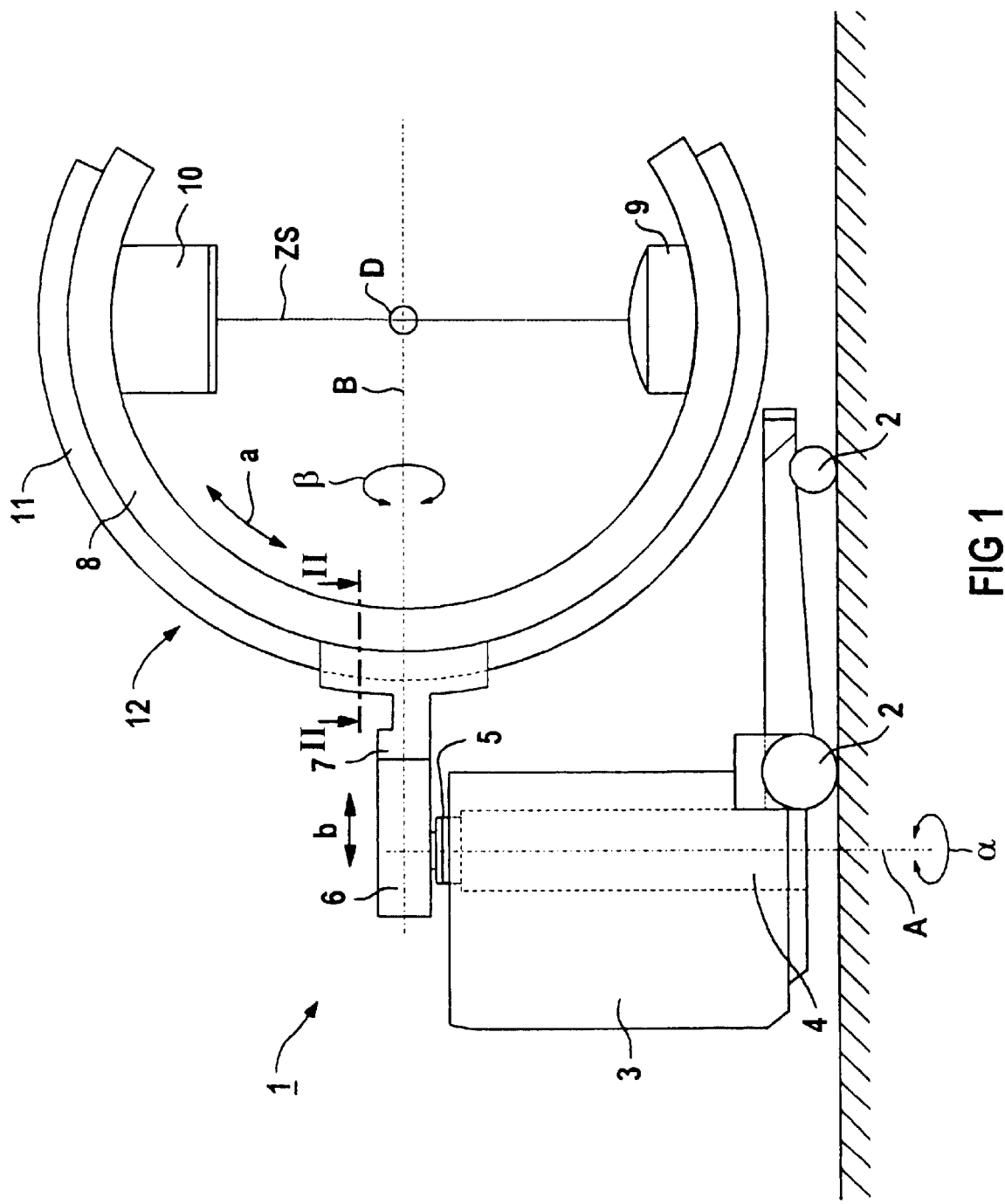
FIG. 1 is a side elevational view of a unit according to the present invention with a handle extending along the mounting side of the carrying arrangement.

The principles of the present invention are particularly useful when incorporated in a C-arm X-ray unit, generally indicated at 1 in FIG. 1. The X-ray unit 1 has a carriage 3 which can be displaced on wheels 2. The C-arm X-ray unit 1 has a lifting arrangement 4 which is merely schematically illustrated in FIG. 1 and has a column 5 with a longitudinal axis A about which the column 5 can be rotated in the direction of the double-arrow α. Arranged on the column 5 is a retaining part 6, on which there is arranged, in turn, a bearing part 7 for mounting a carrying arrangement designed as a C-arm 8. The C-arm 8 has an X-ray source 9 and an X-ray receiver 10, which are mounted opposite one another at fastening points on an inner circumferential side inward of the ends of the C-arm 8, so that the central ray ZS of a bundle of X-rays which originates from the X-ray source 9 strikes the detector surface of the X-ray receiver 10 more or less centrally.

The bearing part 7 is mounted on the retaining part 6 in a manner known per se so that it can be rotated about a common axis B of the retaining part 6 and of the bearing part 7, as illustrated by the double-arrow β, and can be displaced in the direction of the axis B, as illustrated by the double-arrow b. The C-arm 8 is mounted on the bearing part 7 so that it can be displaced relative to the bearing part 7 along the circumference of the C-arm in the direction of the double-arrow a. With the aid of the lifting arrangement 4, the C-arm 8, which is connected to the column 5 of the lifting arrangement 4 by the bearing part 7 and the retaining part 6, can be adjusted vertically relative to the carriage 3.

The adjustment of the C-arm 8 in the bearing part 7 preferably takes place isocentrically, for example, the point of rotation D of the C-arm 8 is located in the path of the central ray ZS of the bundle of X-rays which originates from the X-ray source 9.

For the manual adjustment of the C-arm 8 along its circumference relative to the bearing part 7; for the adjustment of the C-arm about the axis B and along the axis B; and for the vertical adjustment of the C-arm 8 by an individual (not illustrated in the FIG. 1), the C-arm 8 is provided with a handle 11. The handle 11 is arranged at least essentially centrally on the outer circumferential side 12 of the C-arm 8, which circumferential side is the mounting side of the C-arm 8 in relation to the bearing part 7 and extends beyond the fastening points for the X-ray source and the X-ray receiver.

Figure 2:
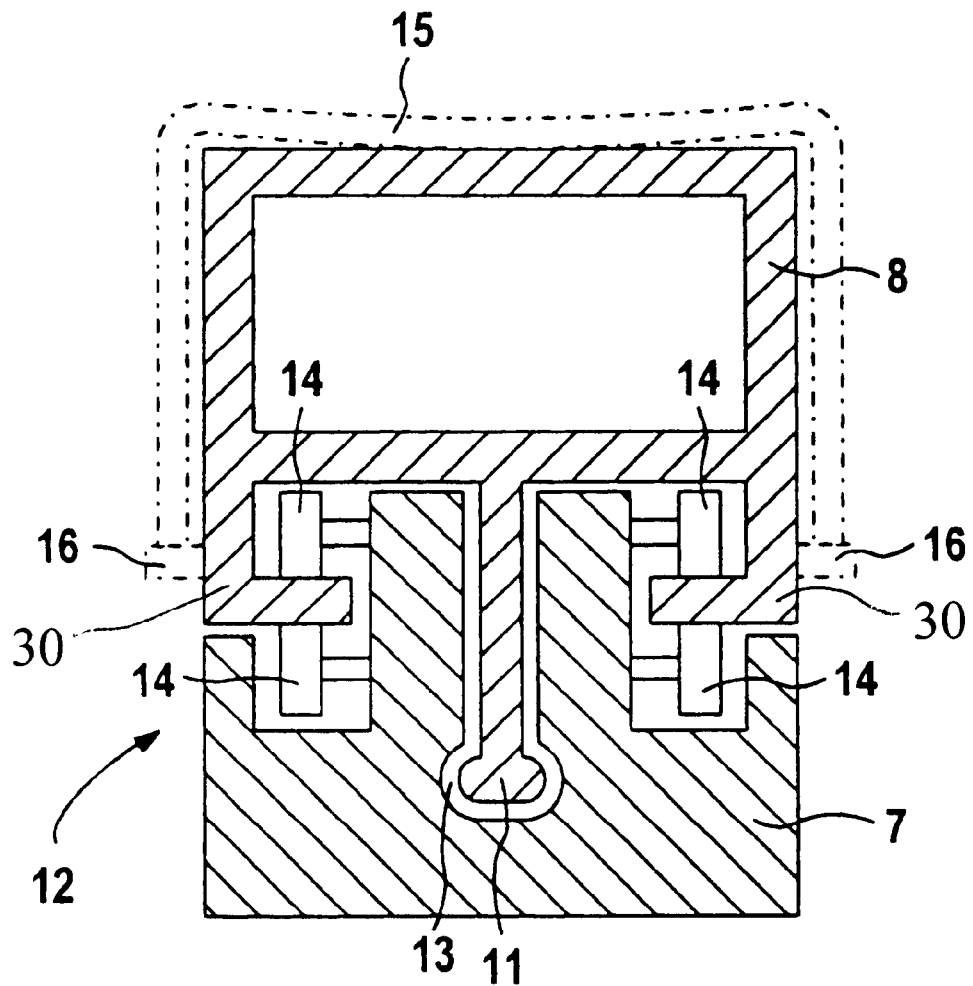
FIG. 2 is a cross-sectional view taken along the lines II—II of FIG. 1.

During adjustment of the C-arm 8 relative to the bearing part 7, the handle 11 moves through the bearing part 7, which is provided with a cutout 13 for this purpose. FIG. 2, which shows the cross-section of FIG. 1, illustrates schematically the mounting of the C-arm 8 in relation to the outer circumferential side 12 of the arm with a pair of L-shaped roller tracks 30 being engaged by rollers 14 of the bearing part 7. The part 7 has a cutout 13 for the handle 11 of the C-arm 8. By virtue of the handle 11 being arranged on the mounting side 12 of the C-arm 8, the handle no longer adds to the width of the C-arm 8. As a result, obstructions caused by the handle during operation of the unit are avoided.

Furthermore, by virtue of being arranged on the outer circumferential side 12 of the C-arm 8, the handle 11, in the manner indicated schematically in FIG. 2, following a sterile covering of the C-arm 8 by a sterile sheet material 15, which is fastened on the C-arm 8, for example by snap fasteners 16, is not concealed by the sheet material 15. Thus, the handle 11 is easily accessible to the individual for the adjustment of the C-arm 8 relative to the bearing part 7.

In the case of the present exemplary embodiment, the handle 11, as can be seen from FIG. 1, extends through the bearing part 7 along the outer circumferential side 12 of the C-arm 8. The handle 11 here is designed as a continuous handle surface, for example the handle does not have any webs or relatively large openings through which objects or body parts can pass. This prevents the situation where, during adjustments of the C-arm 8 relative to the bearing part 7, a body part, in particular an operator's hand, which could otherwise pass undesirably between the handle and the bearing part 7, gets caught.

Figure 3:
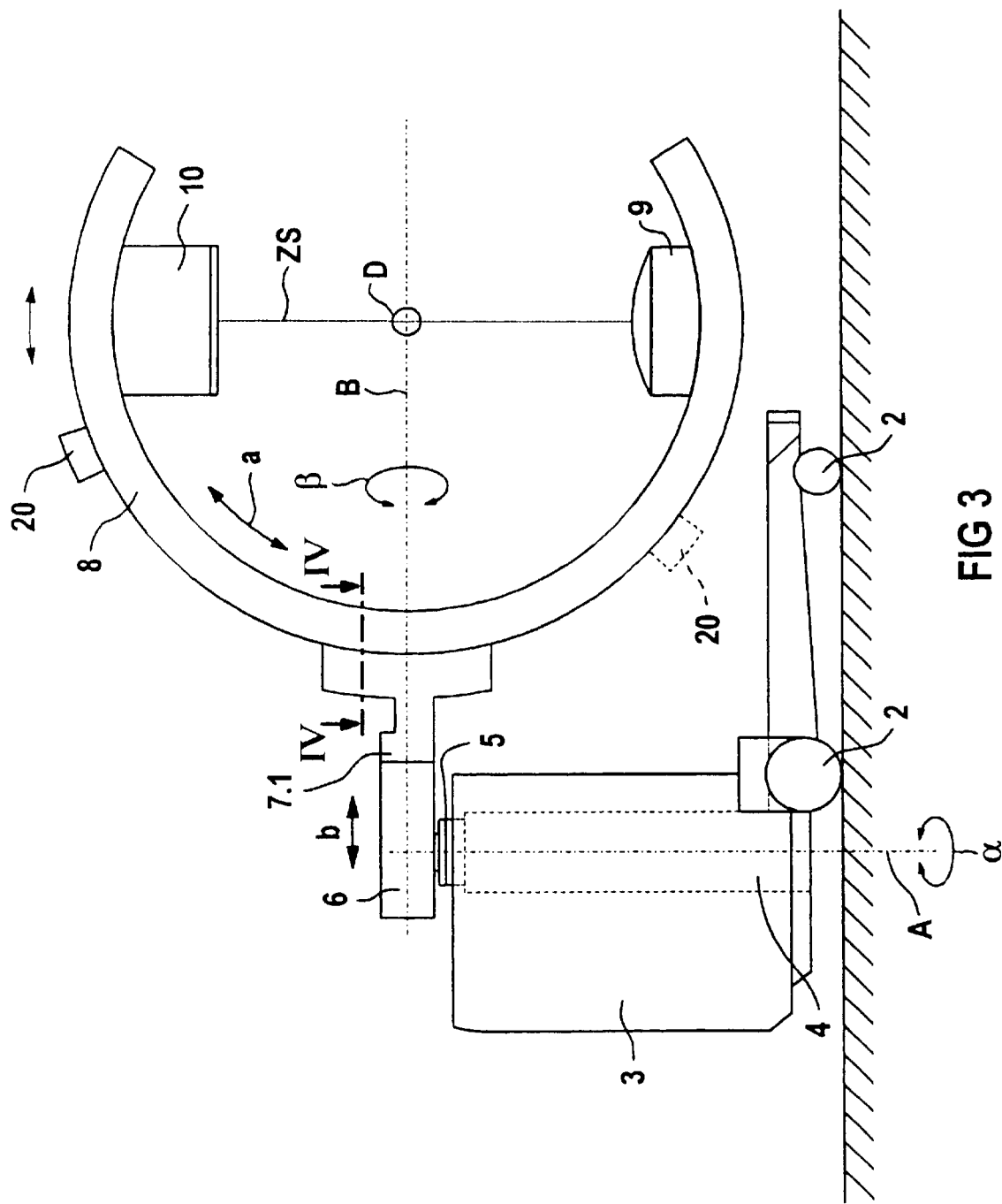
FIG. 3 is a side elevational view of a unit according to the present invention with a handle which can be displaced along the mounting side of the carrying arrangement.

A second embodiment of the unit according to the invention is illustrated in FIG. 3 and is likewise designed as a C-arm X-ray unit. The C-arm X-ray unit shown in FIG. 3 is largely identical in structure and functional terms to the C-arm X-ray unit 1 shown in FIG. 1, Those components of the C-arm X-ray unit shown in FIG. 3 which correspond to components of the C-arm X-ray unit 1 shown in FIG. 1 are provided with the same designation.

Figure 4:
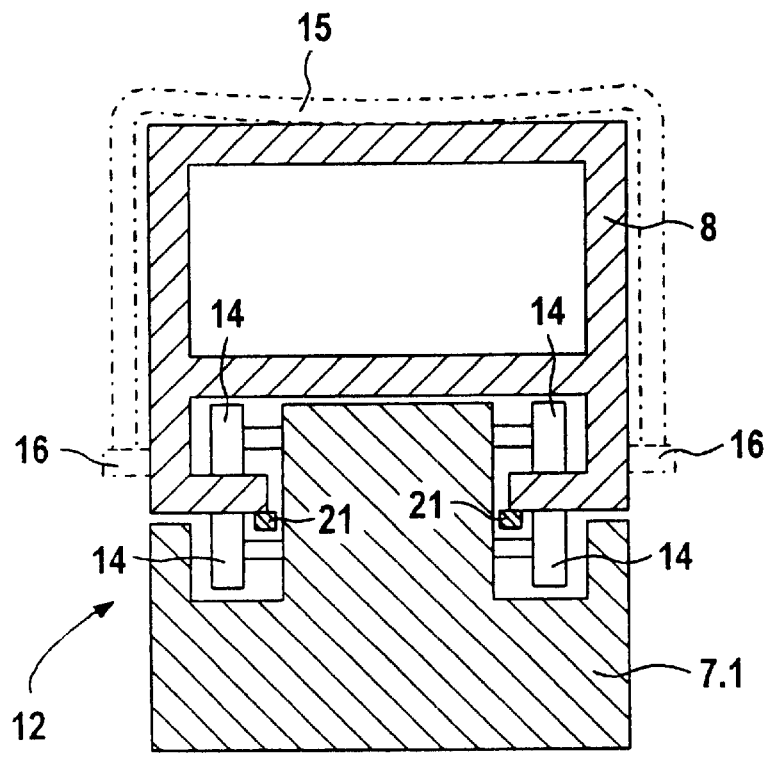
FIG. 4 is a cross-sectional view taken along the lines IV—IV of FIG. 3.

Unlike the C-arm X-ray unit 1 of FIG. 1, the C-arm X-ray unit shown in FIG. 3, instead of having the handle 11 which extends through the bearing part and along the outer circumferential side 12 of the C-arm 8, has a handle 20 which can be adjusted along the outer circumferential side 12 of the C-arm 8. In the case of the present exemplary embodiment, the bearing part 7.1 of the C-arm X-ray unit is not provided with a cutout for the through-passage of the handle 20. As can be seen from FIG. 4, the handle 20 is guided on rails 21 arranged along the outer circumferential side 12 of the C-arm 8 and the handle is provided with means for arresting or holding it on the rails 21, for example with clamping means which are known per se and can be actuated by virtue of a button or a lever provided on the handle 20 being actuated. In this way, the handle can be moved by an operator into a desired position on the outer circumferential side 12 of the C-arm 8 and fixed there. Thus, it is possible for the handle 20 to be used for adjusting the C-arm 8 relative to the bearing part 7.

In the case of the present exemplary embodiment, the handle 20 is arranged on the outer circumferential side 12 of the C-arm 8 adjacent the X-ray receiver 10. It is also possible, however, in the manner indicated in FIG. 3, for such a handle to be arranged on the outer circumferential side 12 of the C-arm 8 adjacent the X-ray source 9, as illustrated in broken lines.

The handle 11 and the handle 20 need not necessarily be arranged at least essentially centrally on the outer circumferential side of the C-arm 8. Rather, it is also possible, if expedient, for the handles 11 and 20 to be arranged eccentrically on the outer circumferential side of the C-arm 8.

In addition, there is no need for the C-arm of the C-arm X-ray unit to be isocentrically adjustable.

The above-described invention has been explained using the example of a medical unit in the form of a C-arm X-ray unit. However, the unit according to the invention need not necessarily be a medical unit.

Figure 5:
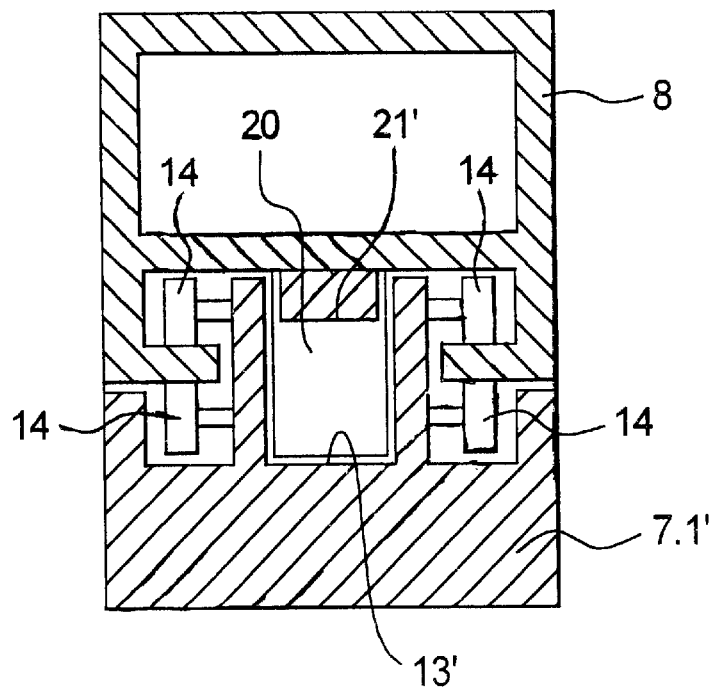
FIG. 5 is a cross-sectional view similar to FIG. 4 of a modification of a bearing part for the carrying arrangement.

In addition, in the context of the invention, mixtures of the two embodiments shown in FIGS. 1 and 2 and FIGS. 3 and 4 are possible. It is, thus, also possible for the bearing part 7.1' (see FIG. 5) to be provided with a cutout 13' for the through-passage of the handle 20 and rail 21' through the bearing part 7.1'.

Although various minor modifications may be suggested by those versed in the art, it should be understood that I wish to embody within the scope of the patent granted hereon all such modifications as reasonably and properly come within the scope of my contribution to the art.

I claim:

1. An X-ray unit having an X-ray source, an X-ray receiver, a bearing part and a carrying arrangement, said carrying arrangement being a C-arm with ends and a mounting side of the C-arm being an outer circumferential side of the C-arm, said C-arm being mounted by the mounting side on the bearing part so that it can be adjusted relative to the bearing part, said C-arm having an inner circumferential side, the X-ray source and X-ray receiver being mounted opposite each other at fastening points on the inner circumferential side inward of the ends, said carrying arrangement being provided with a handle for the manual adjustment of the carrying arrangement relative to the bearing part, said handle being arranged on the mounting side of the carrying arrangement to extend along the outer circumferential side beyond the fastening points for the X-ray source and the X-ray receiver and the bearing part having a cutout portion through which the handle passes during adjustment of the C-arm on the housing part.

2. A unit according to claim 1, wherein the handle is arranged centrally on the mounting side of the C-arm.

3. A unit having a bearing part and a carrying arrangement, said carrying arrangement being a C-arm with a mounting side of the C-arm being an outer circumferential side of the C-arm having a pair of L-shaped roller tracks extending therefrom, said C-arm being mounted by the mounting side on the bearing part with rollers of the bearing part engaging the roller tracks, so that it can be adjusted relative to the bearing part, said carrying arrangement being provided with a handle for the manual adjustment of the carrying arrangement relative to the bearing part, said handle being arranged on the mounting side of the carrying arrangement to extend along the outer circumferential side of the C-arm between the roller tracks and the bearing part having a cutout portion extending between the rollers for receiving the handle, so that the handle passes through the cutout portion during adjustment of the C-arm on the housing part.

4. A unit according to claim 3, wherein the unit is a medical unit.

5. A unit according to claim 3, which is an X-ray unit.

6. A unit according to claim 3, wherein the handle is designed as a handle surface.

7. A unit according to claim 6, wherein the unit is an X-ray unit.

8. A unit having a bearing part and a carrying arrangement, said carrying arrangement being a C-arm with a mounting side of the C-arm being an outer circumferential side of the C-arm, said C-arm being mounted by the mounting side on the bearing part so that it can be adjusted relative to the bearing part, said carrying arrangement being provided with a handle for the manual adjustment of the carrying arrangement relative to the bearing part, said handle being arranged on the mounting side of the carrying arrangement and said handle being displaceable along the mounting side of the C-arm.

9. A unit according to claim 8, wherein the unit is a medical unit.

10. A unit according to claim 8, which is an X-ray unit.

11. A unit according to claim 8, wherein the handle is arranged centrally on the mounting side of the C-arm.

12. A unit according to claim 11, wherein the unit is an X-ray unit.

13. A unit having a bearing part and a carrying arrangement which is mounted by a mounting side on the bearing part so that it can be adjusted relative to the bearing part, said carrying arrangement being provided with a handle for the manual adjustment of the carrying arrangement relative to the bearing part, said handle being adjustably mounted for displacement on the mounting side of the carrying arrangement, and the bearing part having a cutout so that during adjustment of the carrying arrangement relative to the bearing part, the handle can pass through the bearing part.

14. A unit according to claim 13, wherein the carrying arrangement is a C-arm with the mounting side of the C-arm being an outer circumferential side of the C-arm.

15. A unit according to claim 13, wherein the unit is a medical unit.

16. A unit according to claim 13, wherein the unit is an X-ray unit.

* * * * *